United States Patent
Rafaeli et al.

(10) Patent No.: US 7,023,954 B2
(45) Date of Patent: Apr. 4, 2006

(54) OPTICAL ALIGNMENT OF X-RAY MICROANALYZERS

(75) Inventors: Tzachi Rafaeli, Givat Shimshit (IL); Isaac Mazor, Haifa (IL)

(73) Assignee: Jordan Valley Applied Radiation Ltd., Migdal Ha'emek (IL)

( * ) Notice: Subject to any disclaimer, the term of this patent is extended or adjusted under 35 U.S.C. 154(b) by 0 days.

(21) Appl. No.: 10/673,996

(22) Filed: Sep. 29, 2003

(65) Prior Publication Data

US 2005/0069090 A1   Mar. 31, 2005

(51) Int. Cl.
*G01N 23/223* (2006.01)

(52) U.S. Cl. .......................... 378/43; 378/45; 378/50; 378/206

(58) Field of Classification Search ............ 378/43–50, 378/79, 205, 206
See application file for complete search history.

(56) References Cited

U.S. PATENT DOCUMENTS

| | | | | |
|---|---|---|---|---|
| 3,156,824 A | * | 11/1964 | Peyser ........................ 378/157 |
| 3,256,431 A | | 6/1966 | Fraser ........................ 250/43.5 |
| 3,581,087 A | | 5/1971 | Brinkerhoff ................ 250/51.5 |
| 3,980,568 A | | 9/1976 | Pitchford et al. ........... 250/276 |
| 4,521,905 A | * | 6/1985 | Hosokawa ................... 378/206 |
| 4,799,246 A | * | 1/1989 | Fischer ........................ 378/50 |
| 4,852,135 A | | 7/1989 | Anisovich et al. ............ 378/49 |
| 5,351,279 A | * | 9/1994 | She et al. ..................... 378/43 |
| 5,497,008 A | | 3/1996 | Kumakhov .............. 250/505.1 |
| 5,619,548 A | | 4/1997 | Koppel |
| 5,778,039 A | | 7/1998 | Hossain et al. ................ 378/45 |
| 5,812,631 A | | 9/1998 | Yan et al. ..................... 378/85 |
| 5,937,026 A | | 8/1999 | Satoh ........................... 378/44 |
| 6,038,280 A | * | 3/2000 | Rossiger et al. .............. 378/50 |
| 6,108,398 A | | 8/2000 | Mazor et al. ................. 378/45 |
| 6,370,221 B1 | * | 4/2002 | Kaiser et al. ................. 378/45 |
| 6,404,846 B1 | * | 6/2002 | Hasegawa et al. ............ 378/44 |
| 6,453,006 B1 | | 9/2002 | Koppel et al. |
| 6,507,634 B1 | | 1/2003 | Koppel et al. |
| 6,643,354 B1 | | 11/2003 | Koppel et al. |
| 6,711,232 B1 | | 3/2004 | Janik |
| 6,744,950 B1 | | 6/2004 | Aleksoff |

(Continued)

FOREIGN PATENT DOCUMENTS

DE      19705732 A1   10/1997

OTHER PUBLICATIONS

*Brochure:* Capillary Optics, by X-Ray Capillary Optics AB, Sweden 1995.

(Continued)

*Primary Examiner*—Craig E. Church
*Assistant Examiner*—Thomas R. Artman
(74) *Attorney, Agent, or Firm*—Weingarten, Schurgin, Gagnebin & Lebovici LLP

(57) ABSTRACT

A method for X-ray analysis of a sample includes aligning an optical radiation source with an X-ray excitation source, so that a spot on the sample that is irradiated by an X-ray beam generated by the X-ray excitation source is illuminated with optical radiation generated by the optical radiation source. Optical radiation that is reflected from the sample is used to generate a first signal, which is indicative of an alignment of the spot on the sample. The X-ray beam is aligned, responsively to the first signal, so that the spot coincides with a target area of the sample. X-ray photons received from the spot on the sample, after aligning the X-ray beam, are used in generating a second signal that is indicative of a characteristic of the target area.

12 Claims, 2 Drawing Sheets

U.S. PATENT DOCUMENTS

| | | | |
|---|---|---|---|
| 6,810,106 B1 * | 10/2004 | Sato | 378/50 |
| 6,885,726 B1 * | 4/2005 | Uehara et al. | 378/44 |
| 2002/0097837 A1 | 7/2002 | Fanton et al. | |
| 2002/0110218 A1 | 8/2002 | Koppel et al. | |
| 2004/0052330 A1 | 3/2004 | Koppel et al. | |

OTHER PUBLICATIONS

N. Yamamoto, "A Micro-Fluorescent/Diffracted X-Ray Spectrometer With A Micro-X-Ray Beam Formed By A Fine Glass Capillary", Rev. Sci. Instrum. 67(9), Sep. 1996, pp. 3051,3054-3056,3062.

B.J. Cross, et al., "X-Ray Microfluorescence Analyzer For Multilayer Metal Films", Thin Solid 166 (1988), pp. 263-272.

Shimomura, et al., "Annular-Type Solid State Detector For A Scanning X-Ray Analytical Microscope", Rev. Sci. Instrum. 66(9) (Sep. 1995), pp. 4544-4546.

Longoni et al., "A New XRF Spectrometer Based on a Ring-Shaped Multi-Element Silicon Drift Detector and on X-Ray Capillary Optics", IEEE Transactions on Nuclear Science 49:3 (2002), pp. 1001-1005.

* cited by examiner

OPTICAL ALIGNMENT OF X-RAY MICROANALYZERS

FIELD OF THE INVENTION

The present invention relates generally to instruments for X-ray analysis, and specifically to methods and devices for aligning such instruments to analyze a target area of a sample.

BACKGROUND OF THE INVENTION

X-ray microanalyzers use an X-ray beam to irradiate a small spot on a sample. The microanalyzer then detects X-rays that are emitted from the spot, by reflection, scattering or fluorescence, in order to determine properties of the sample with fine spatial resolution.

For example, U.S. Pat. No. 6,108,398, whose disclosure is incorporated herein by reference, describes an X-ray microfluorescence analyzer. A sample is irradiated with X-rays through a polycapillary optic, which focuses the X-ray beam to a spot about 50 µm in diameter. Multiple X-ray detectors, such as silicon PIN diodes, are arranged in a ring, centered over the spot, in order to capture the emitted fluorescent photons over a large range of angles. The X-ray detectors produce electrical signals in response to the incident photons. These signals are analyzed in order to determine the spectrum and intensity of the X-ray photons, which are indicative of characteristics of the sample at the spot, including its composition and layer thickness. The sample may be scanned horizontally relative to the analyzer (or the analyzer may be scanned over the sample) in order to measure the microfluorescence at different points on the sample.

SUMMARY OF THE INVENTION

X-ray microanalyzers are useful for analyzing characteristics of small features on samples, such as circuit elements deposited on semiconductor wafers. The sizes of these elements may be substantially less than 1 mm. Accurate alignment of the X-ray spot with the feature of interest is therefore important but may be difficult to achieve. In response to this need, embodiments of the present invention provide X-ray microanalyzers having an optical observation channel, which is aligned with the X-ray source and enables the X-ray spot to be precisely aligned with features of interest on the sample.

There is therefore provided, in accordance with an embodiment of the present invention, apparatus for X-ray analysis of a sample, including:

an X-ray excitation source, which is arranged to irradiate a spot on the sample with an X-ray beam;

one or more X-ray detectors, which are arranged so as to define a ring around the spot, the ring having a gap therein, and which are adapted to receive X-ray photons from the spot on the sample and to generate a first signal in response to the photons that is indicative of a characteristic of the sample;

an optical radiation source, which is aligned with the X-ray excitation source so as to illuminate the spot on the sample with optical radiation; and an optical detector, which is positioned in the gap in the ring so as to receive the optical radiation that is reflected from the sample, and to generate a second signal that is indicative of an alignment of the spot with a target area of the sample.

In one embodiment, the X-ray beam causes the sample to emit fluorescent X-ray photons, which are received by the one or more X-ray detectors, and the first signal is indicative of a composition of a feature of the sample in the target area.

In an aspect of the invention, the optical radiation source is arranged to illuminate the spot from a position within the gap in the ring. In another aspect of the invention, the X-ray excitation source includes an X-ray optic, which is arranged to focus the X-ray beam onto the spot on the sample, and the optical radiation source and the X-ray optic are configured so that the optical radiation is also focused onto the spot by the X-ray optic.

Typically, the apparatus includes a controller, which is adapted to align the X-ray excitation source with the sample responsively to the second signal, so that the spot is incident on the target area.

There is also provided, in accordance with an embodiment of the present invention, apparatus for X-ray analysis of a sample, including:

an X-ray excitation source, which is adapted to generate an X-ray beam;

an optical radiation source, which is adapted to generate optical radiation;

an X-ray optic, which is arranged to focus both the X-ray beam and the optical radiation onto a spot on the sample;

one or more X-ray detectors, which are adapted to receive X-ray photons from the spot on the sample, and to generate a first signal in response to the photons that is indicative of a characteristic of the sample; and an optical detector, which is arranged to receive the optical radiation that is reflected from the spot on the sample, and to generate a second signal that is indicative of an alignment of the spot with a target area of the sample.

In one embodiment, the X-ray optic includes a polycapillary optic.

The apparatus may include a movable reflector, which is positionable to direct the optical radiation toward the X-ray optic during the alignment of the spot with the feature, and which is repositionable to permit the X-ray beam to impinge on the X-ray optic after the alignment is completed.

There is additionally provided, in accordance with an embodiment of the present invention, apparatus for X-ray analysis of a sample, including:

an X-ray excitation source, which is arranged to irradiate a spot on the sample with an X-ray beam;

an X-ray detector, which is adapted to receive X-ray photons from the spot on the sample, and to generate a first signal in response to the photons that is indicative of a characteristic of the sample;

an optical radiation source, which is aligned with the X-ray excitation source so as to illuminate the spot on the sample with optical radiation; and an optical detector, which is arranged to receive the optical radiation that is reflected from the sample, and to generate a second signal that is indicative of an alignment of the spot with a target area of the sample.

There is further provided, in accordance with an embodiment of the present invention, a method for X-ray analysis of a sample, including:

aligning an optical radiation source with an X-ray excitation source, so that a spot on the sample that is irradiated by an X-ray beam generated by the X-ray excitation source is illuminated with optical radiation generated by the optical radiation source;

receiving the optical radiation that is reflected from the sample, and responsively to the received optical radiation, generating a first signal that is indicative of an alignment of the spot on the sample;

aligning the X-ray beam, responsively to the first signal, so that the spot coincides with a target area of the sample; and receiving X-ray photons from the spot on the sample after aligning the X-ray beam, and responsively to the received X-ray photons, generating a second signal that is indicative of a characteristic of the target area.

In one embodiment, aligning the optical radiation source includes irradiating an alignment target with the X-ray beam, so as to cause the target to emit light from a point on the target at which the X-ray beam is incident, and aligning the optical radiation source with the point on the target.

The present invention will be more fully understood from the following detailed description of the embodiments thereof, taken together with the drawings in which:

DETAILED DESCRIPTION OF EMBODIMENTS

Figure 1A:
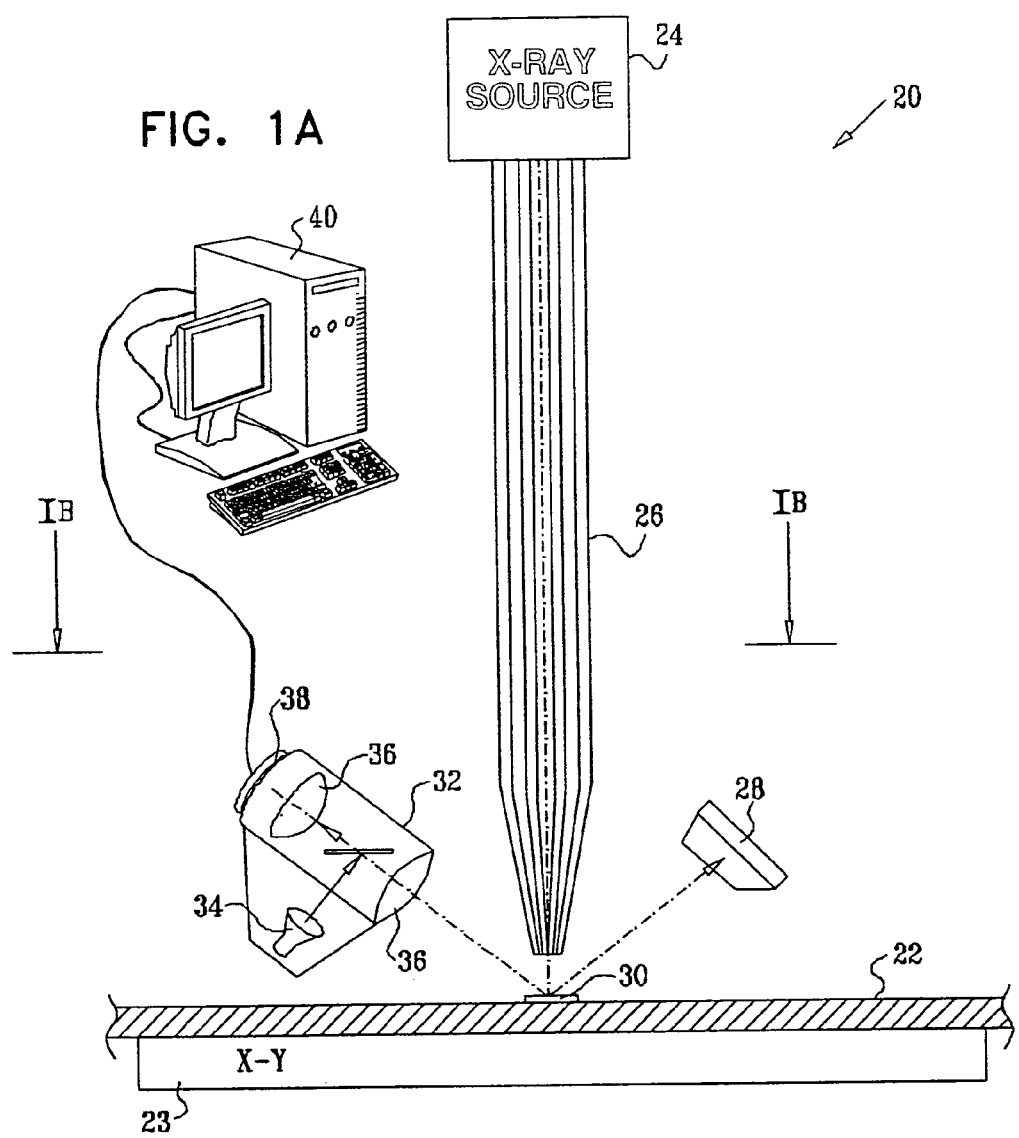
FIG. 1A is a schematic side view of an X-ray microanalyzer with an optical alignment channel, in accordance with an embodiment of the present invention.
Figure 1B:
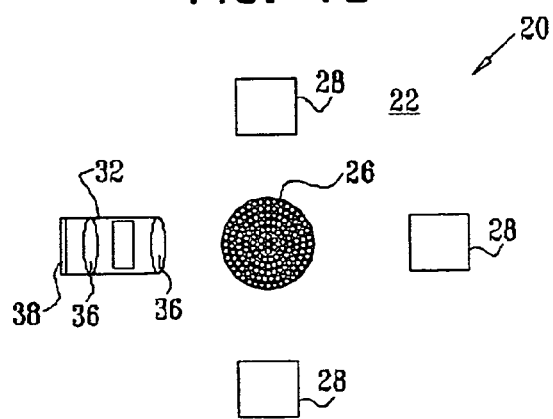
FIG. 1B is a schematic, sectional view showing a detail of the microanalyzer of FIG. 1A.

Reference is now made to FIGS. 1A and 1B, which schematically illustrate an X-ray microanalyzer 20, for analysis of a sample 22, in accordance with an embodiment of the present invention. FIG. 1A is a side view of the microanalyzer, while FIG. 1B is a sectional view, taken along a line IB—IB in FIG. 1A, looking downward toward sample 22. The sample is typically planar, such as a semiconductor wafer, and is mounted on a motion stage 23. Alternatively, the sample may be stationary, and another motion device (not shown) may be used to move the elements of the microanalyzer relative to the sample.

Microanalyzer 20 comprises an X-ray source 24, typically an X-ray tube, which irradiates a small spot on sample 22 with a beam of X-rays. In the exemplary embodiments shown here, a polycapillary X-ray optic 26 is used to focus the X-rays onto the sample, as described in the above-mentioned U.S. Pat. No. 6,108,398. Alternatively, X-ray optics of other types, as are known in the art, may be used for beam focusing. Sample 22 is positioned so that the X-ray spot impinges on a target area 30 on sample 22. The target area typically comprises a particular feature of interest, such as a metal pad or plug formed on a semiconductor wafer. Target area 30 emits X-ray fluorescence, and the fluorescent X-ray photons are collected by an array of X-ray detectors 28, which are arranged in a ring, as described, for example, in U.S. Pat. No. 6,108,398. Alternatively or additionally, the X-ray detectors may be used to detect scattering or reflection of X-rays from sample 22. The X-ray detectors generate signals, which are processed, as is known in the art, in order to determine characteristics of target area 30.

Although microanalyzer 20 includes three X-ray detectors 28 detectors in a ring around the X-ray spot (as shown in FIG. 1B), the ring may alternatively include larger or smaller numbers of X-ray detectors. Further alternatively, instead of using several discrete X-ray detectors, a monolithic detector ring may be positioned around X-ray optic 26. Detector rings of this sort are described, for example, by Shimomura et al., in "Annular-type Solid State Detector for a Scanning X-ray Analytical Microscope," *Review of Scientific Instruments* 66:9 (1995), pages 4544–4546, and by Longoni et al., in "A New XRF Spectrometer Based on a Ring-Shaped Multi-Element Silicon Drift Detector and on X-Ray Capillary Optics," *IEEE Transactions on Nuclear Science* 49:3 (2002), pages 1001–1005.

To facilitate alignment of the X-ray spot from source 24 on target area 30, microanalyzer 20 comprises an optical alignment assembly 32, which is located in a gap in the ring in place of one of the X-ray detectors (as seen most clearly in FIG. 1B). Alternatively, if a monolithic detector ring is used, a gap may be left in the monolithic ring to accommodate the optical alignment assembly. Assembly 32 comprises a optical radiation source 34, which may emit visible, infrared or ultraviolet radiation. Optics 36 focus the optical radiation from source 34 onto sample 22, and collect the optical radiation that is reflected from the sample onto a suitable optical detector 38. Optics 36 are aligned with X-ray optic 26 so that the beams of X-rays and of optical radiation impinge on substantially the same spot on the sample. Initial alignment of assembly 32 with X-ray optic 26 may be accomplished, for example, using a test target that emits visible light when irradiated with X-rays. The target is irradiated by X-ray source 24 via optic 26, and elements of assembly 32, such as optical radiation source 34, are positioned and adjusted relative to the light emitted from the irradiated spot on the target.

Detector 38 generates a signal in response to the reflected optical radiation, which is input to a system controller 40, typically a computer processor. Controller 40 analyzes the signal in order to determine whether X-ray optic 26 is properly aligned on target area 30. If the controller finds that the X-ray beam is out of alignment, it may drive stage 23 to position the target area properly under the X-ray beam. Alternatively or additionally, the output of assembly 32 may be used to provide an image or other alignment indicator for use by an operator of microanalyzer 20 in adjusting the alignment of the X-ray beam. The optical signal may also be analyzed in order to determine whether the vertical distance between sample 22 and optic 26 is correct, so that the X-ray beam will be properly focused on the target area, and a vertical alignment element (not shown) may be driven to adjust the distance if necessary.

Typically, detector 38 comprises an imaging detector, such as a CCD or CMOS detector array. Optical radiation source 34 and optics 36 are arranged to illuminate an area of sample 22 that is larger than the X-ray spot created by X-ray optic 26 and is approximately centered on the X-ray spot. The electronic image of the sample that is formed by detector 38 includes target area 30. This image is analyzed by controller 40 and/or observed by the operator of the microanalyzer while controlling stage 23 so as to center the target area in the image. A crosshairs or other alignment target may be optically or electronically superimposed on the image formed by detector 38 in order to indicate the point of incidence of the X-ray beam on the sample.

Alternatively, source 34 and optics 36 may be used to create a small spot of optical radiation, which is aligned with the X-ray spot on sample 22 and is comparable in size to the X-ray spot or smaller. In this case, detector 38 need not comprise an imaging detector, and may simply detect the intensity and/or color of the light reflected from the sample. This configuration is useful particularly when target area 30 comprises a feature having different optical characteristics from the surrounding area of sample 22, for example, when the feature of interest is a metal pad surrounded by an area of dielectric material. Controller 40 may then simply drive stage 23 until it reaches a position in which the output signal from detector 38 has a desired, preset level, corresponding to the feature.

Figure 2:
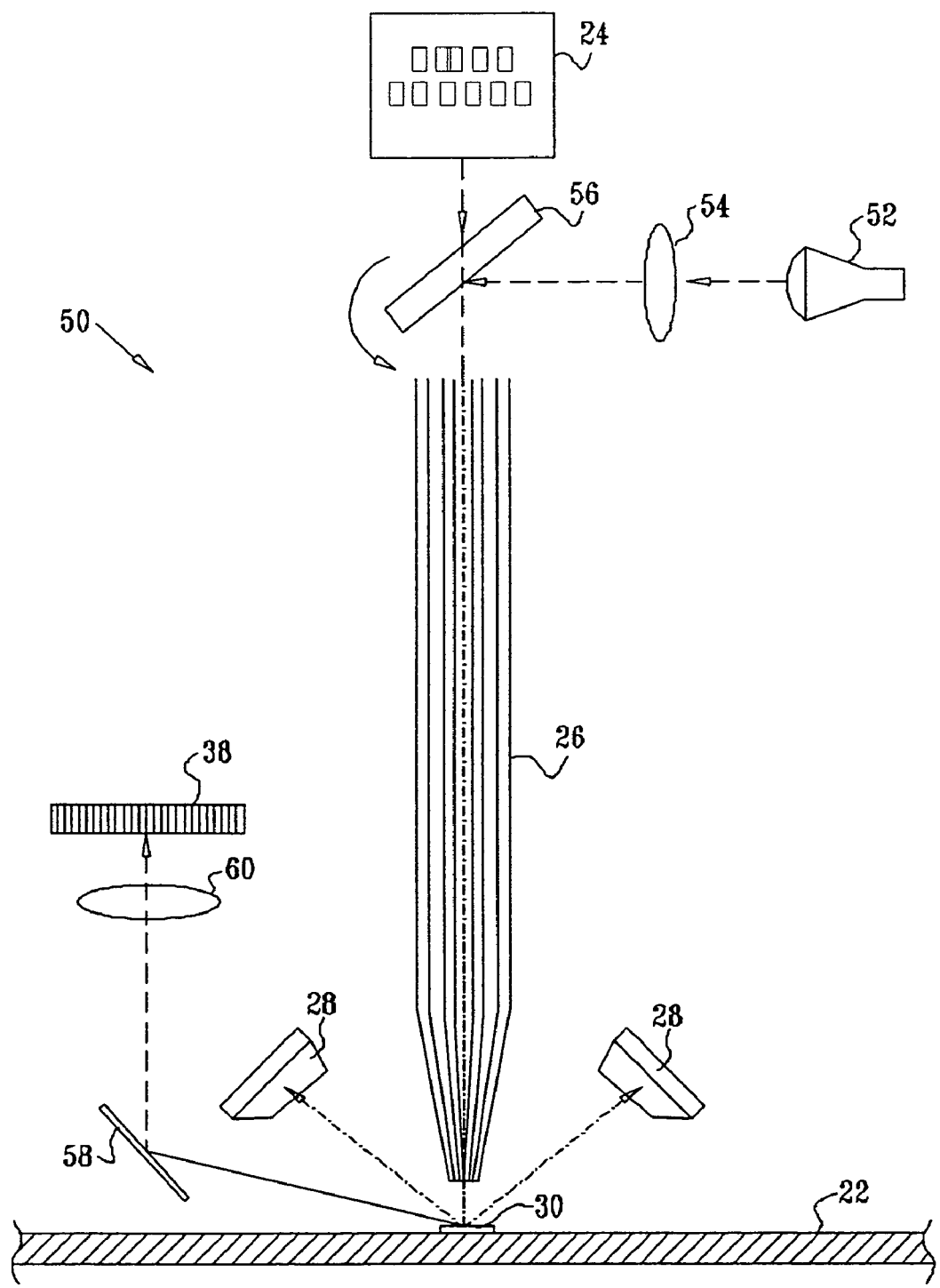
FIG. 2 is a schematic side view of an X-ray microanalyzer with an optical alignment channel, in accordance with another embodiment of the present invention.

FIG. 2 is a schematic side view of an X-ray microanalyzer 50, in accordance with another embodiment of the present invention. In this embodiment, optical radiation emitted by an optical radiation source 52 is focused by illumination optics 54 into X-ray optic 26. The polycapillary optic serves as a light guide for the optical radiation. A movable mirror 56 is used to direct the optical radiation into the X-ray optical path during alignment of the microanalyzer. Once the alignment is complete, mirror 56 is removed from the optical path, allowing X-rays from source 24 to enter the polycapillary. Alternatively, a thin reflecting element, such as a pellicle, which reflects optical radiation but is substantially transparent to X-rays, may be used in place of mirror 56. The coaxial alignment of the X-ray and optical illumination beams may be implemented not only using polycapillary optics as shown here, but also using other types of X-ray optics, such as pinholes and curved focusing elements.

The beam of optical radiation is focused by X-ray optic 26 to a small spot on sample 22, which coincides precisely with the X-ray spot created by source 24. Optical radiation reflected from sample 22 is directed by a mirror 58 and a collection lens 60 onto optical detector 38. The optical detector may comprise an imaging detector or it may simply sense the reflected light level, as described above. Although the reflected radiation is collected at a very low angle, this configuration is nonetheless adequate for aligning microanalyzer 50 with target area 30, because of the precise alignment between the X-ray and optical radiation beams. Alternatively, detector 38 may take the place of one of X-ray detectors 28, as in the configuration of FIGS. 1A and 1B, at the cost of slightly reduced throughput in the X-ray measurements. As a still further alternative, if X-ray detectors 28 are of a type, such as silicon diode detectors, that is also sensitive to optical radiation, then one or more of the X-ray detectors may be coupled to serve as optical detectors, as well.

As a further alternative, optical radiation source 52 may likewise be oriented, with suitable optics, to direct the illuminating beam onto sample 22 at a low angle, so that it is not necessary to block the X-ray beam path while performing optical alignment. Detector 38 may in this case be placed in either the position shown in FIG. 2 or within the ring of X-ray detectors 28, as shown in FIGS. 1A and 1B. Other configurations of optical illumination and detection elements implementing the principles of the present invention will be apparent to those skilled in the art.

Although microanalyzers 20 and 50 are particularly suited for detection of X-ray microfluorescence, the principles of the present invention may similarly be used in optical alignment of other types of X-ray systems, such as systems for X-ray reflectometry and X-ray scattering measurements. It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. Apparatus for X-ray analysis of a sample, comprising:
   an X-ray excitation source, which is arranged to irradiate a spot on the sample with an X-ray beam along a beam axis;
   one or more X-ray detectors, which are arranged so as to define a ring around the spot, the ring having a gap therein at a location that is radially displaced from the beam axis, and wherein the one or more X-ray detectors are adapted to receive X-ray photons from the spot on the sample and to generate a first signal in response to the photons that is indicative of a characteristic of the sample;
   an optical radiation source, which is aligned with the X-ray excitation source so as to illuminate the spot on the sample with optical radiation; and
   an optical detector, which is positioned in the gap in the ring so as to receive the optical radiation that is reflected from the sample, and to generate a second signal that is indicative of an alignment of the spot with a target area of the sample.

2. The apparatus according to claim 1, wherein the X-ray beam causes the sample to emit fluorescent X-ray photons, which are received by the one or more X-ray detectors, and wherein the first signal is indicative of a composition of a feature of the sample in the target area.

3. The apparatus according to claim 1, wherein the optical radiation source is arranged to illuminate the spot from a position within the gap in the ring.

4. The apparatus according to claim 1, wherein the X-ray excitation source comprises an X-ray optic, which is arranged to focus the X-ray beam onto the spot on the sample, and wherein the optical radiation source and the X-ray optic are configured so that the optical radiation is also focused onto the spot by the X-ray optic.

5. The apparatus according to claim 1, and comprising a controller, which is adapted to align the X-ray excitation source with the sample responsively to the second signal, so that the spot is incident on the target area.

6. Apparatus for X-ray analysis of a sample, comprising:
   an X-ray excitation source, which is adapted to generate an X-ray beam;
   an optical radiation source, which is adapted to generate optical radiation;
   an X-ray optic, which is arranged to focus both the X-ray beam and the optical radiation onto a spot on the sample;
   one or more X-ray detectors, which are adapted to receive X-ray photons from the spot on the sample, and to generate a first signal in response to the photons that is indicative of a characteristic of the sample;
   an optical detector, which is arranged to receive the optical radiation that is reflected from the spot on the sample, and to generate a second signal that is indicative of an alignment of the spot with a target area of the sample; and
   a movable reflector, which is positionable to direct the optical radiation toward the X-ray optic during the alignment of the spot with the target area, and which is repositionable to permit the X-ray beam to impinge on the X-ray optic after the alignment is completed.

7. The apparatus according to claim 6, wherein the X-ray beam causes the sample to emit fluorescent X-ray photons, which are received by the one or more X-ray detectors, and wherein the first signal is indicative of a composition of a feature of the sample in the target area.

8. The apparatus according to claim 6, wherein the one or more X-ray detectors are arranged so as to define a ring around the spot.

9. The apparatus according to claim 6, and comprising a controller, which is adapted to align the X-ray optic with the sample responsively to the second signal, so that the spot is incident on the target area.

10. A method for X-ray analysis of a sample, comprising:
aligning an optical radiation source with an X-ray excitation source, so that a spot on the sample that is irradiated by an X-ray beam generated by the X-ray excitation source along a beam axis is illuminated with optical radiation generated by the optical radiation source;
receiving the optical radiation that is reflected from the sample, and responsively to the received optical radiation, generating a first signal that is indicative of an alignment of the spot on the sample;
aligning the X-ray beam, responsively to the first signal, so that the spot coincides with a target area of the sample; and
receiving X-ray photons from the spot on the sample after aligning the X-ray beam, and responsively to the received X-ray photons, generating a second signal that is indicative of a characteristic of the target area,
wherein receiving the X-ray photons comprises arranging one or more X-ray detectors so as to define a ring around the spot, while leaving a gap in the ring at a location that is radially displaced from the beam axis, and
wherein receiving the optical radiation comprises positioning an optical detector in the gap in the ring so as to receive the optical radiation that is reflected from the sample.

11. The method according to claim 10, wherein receiving the X-ray photons comprises receiving fluorescent X-rays, which are emitted by the sample in response to the X-ray beam, so that the second signal is indicative of a composition of a feature of the sample in the target area.

12. A method for X-ray analysis of a sample, comprising:
aligning an optical radiation source with an X-ray excitation source, so that a spot on the sample that is irradiated by an X-ray beam generated by the X-ray excitation source is illuminated with optical radiation generated by the optical radiation source;
receiving the optical radiation that is reflected from the sample, and responsively to the received optical radiation, generating a first signal that is indicative of an alignment of the spot on the sample;
aligning the X-ray beam, responsively to the first signal, so that the spot coincides with a target area of the sample; and
receiving X-ray photons from the spot on the sample after aligning the X-ray beam, and responsively to the received X-ray photons, generating a second signal that is indicative of a characteristic of the target area,
wherein aligning the optical radiation source comprises irradiating an alignment target with the X-ray beam, so as to cause the target to emit light from a point on the target at which the X-ray beam is incident, and aligning the optical radiation source with the point on the target.

* * * * *